United States Patent
Wong

Patent Number: 5,222,389
Date of Patent: Jun. 29, 1993

[54] MULTI-CHANNEL GAS SAMPLE CHAMBER

[75] Inventor: Jacob Y. Wong, Santa Barbara, Calif.

[73] Assignee: Gaztech International Corporation, Goleta, Calif.

[21] Appl. No.: 816,596

[22] Filed: Dec. 31, 1991

Related U.S. Application Data

[63] Continuation-in-part of Ser. No. 793,990, Nov. 18, 1991, Pat. No. 5,163,332, which is a continuation of Ser. No. 604,615, Oct. 26, 1990, abandoned, which is a continuation-in-part of Ser. No. 503,216, Apr. 2, 1990, Pat. No. 5,060,508.

[51] Int. Cl.⁵ .............................. G01N 1/00
[52] U.S. Cl. .................... 73/31.02; 356/437
[58] Field of Search ......... 73/863.23, 863.81, 864.81, 73/31.01, 31.02, 31.05; 250/338.5, 343, 344–346, 436; 356/437, 440; 340/632

[56] References Cited

U.S. PATENT DOCUMENTS

| | | | |
|---|---|---|---|
| 3,966,439 | 6/1976 | Vennos | 73/863.22 |
| 4,047,437 | 9/1977 | Brooks | 73/863.33 |
| 4,155,247 | 5/1979 | Kacmarek et al. | 73/863.23 |
| 4,507,558 | 3/1985 | Bonne | 250/345 |
| 4,709,150 | 11/1987 | Burough et al. | 250/338.5 |
| 4,749,276 | 6/1988 | Bragg et al. | 250/343 |
| 4,800,272 | 1/1989 | Harley et al. | 250/255 |
| 4,947,578 | 8/1990 | Anderson et al. | D22/122 |
| 5,163,332 | 11/1992 | Wong | 356/437 |

FOREIGN PATENT DOCUMENTS

| | | | |
|---|---|---|---|
| 0039049 | 3/1980 | Japan | 356/438 |
| 0173734 | 10/1984 | Japan | 356/437 |
| 0105947 | 6/1985 | Japan | 356/437 |
| 0298031 | 12/1988 | Japan | 356/437 |

*Primary Examiner*—Robert Raevis
*Attorney, Agent, or Firm*—Daniel C. McKown

[57] ABSTRACT

A gas sample chamber for use in a gas analyzer consists of an elongated hollow tube having an inwardly-facing specularly-reflective surface that permits the tube to function also as a light pipe for conducting radiation from a source to a detector through the sample gas. A number of apertures in the wall of the elongated hollow tube permit the sample gas to enter and exit. Particles of smoke and dust of a size greater than 0.1 micron are kept out of the chamber by use of a semi-permeable membrane that spans the apertures in the hollow tube. Condensation of the sample gas components is prevented by heating the sample chamber electrically to a temperature above the dew point of the component of concern. In one embodiment, at least one detector are spaced around the periphery of the elongated hollow tube adjacent one end of it. In another embodiment, at least one detector are spaced along the length of the elongated hollow tube.

6 Claims, 2 Drawing Sheets

FIG. 1
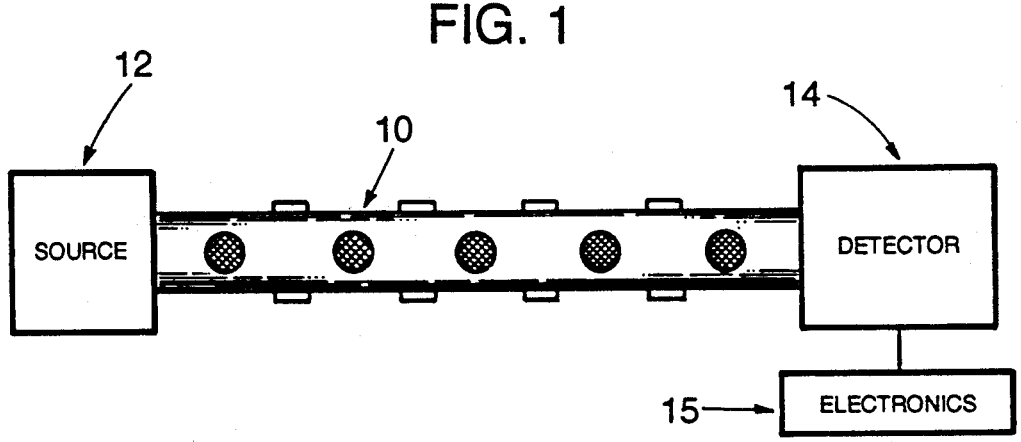
FIG. 2
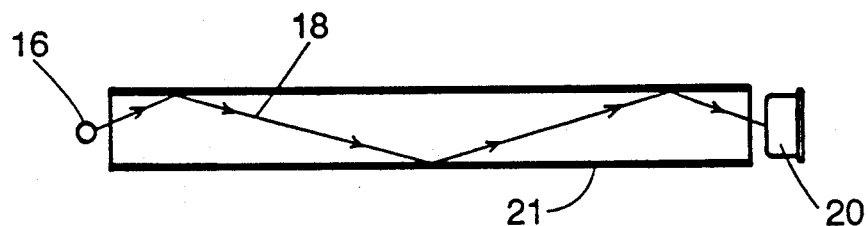
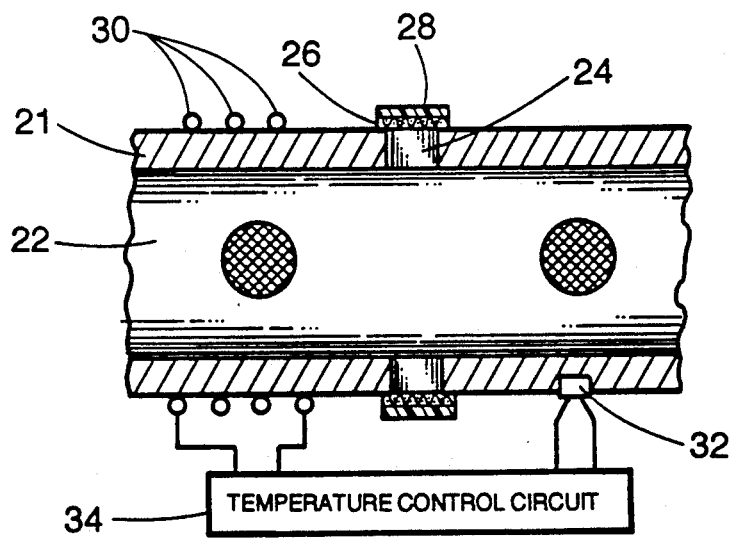
FIG. 3

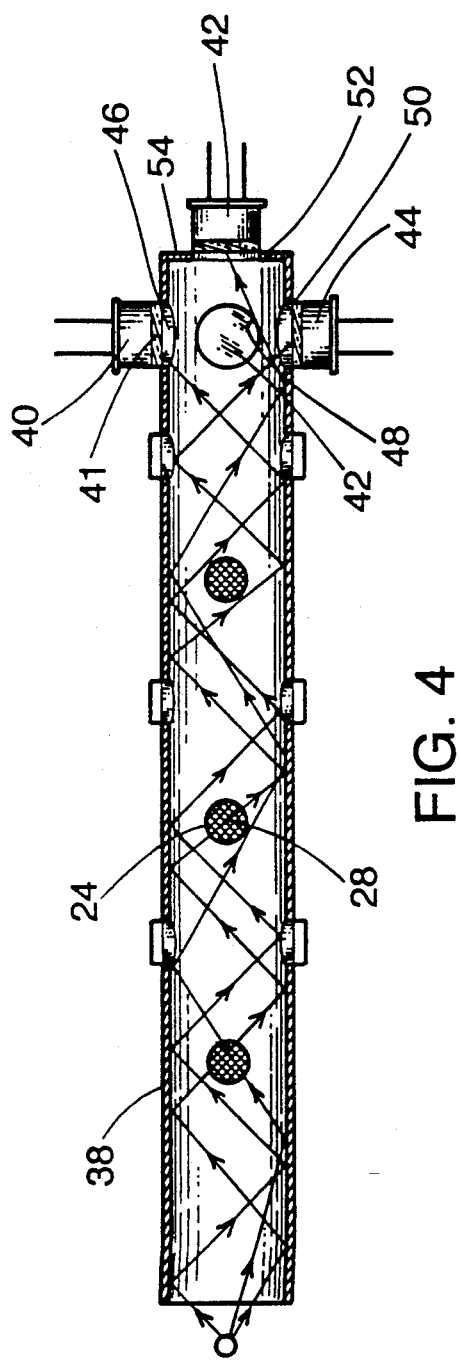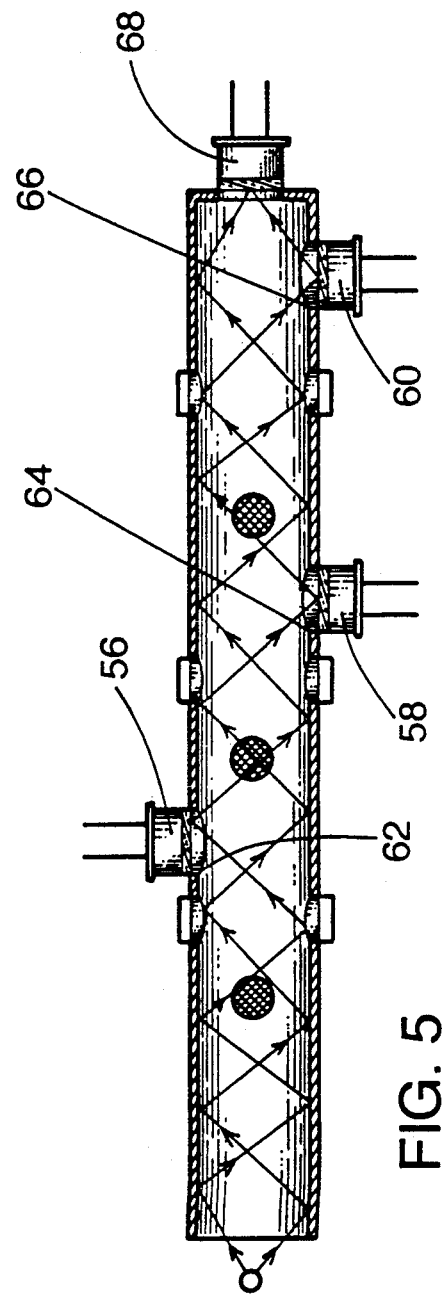

MULTI-CHANNEL GAS SAMPLE CHAMBER

REFERENCE TO RELATED APPLICATIONS

This application is a continuation-in-part of U.S. patent application Ser. No. 07/793,990, filed Nov. 18, 1991 for IMPROVED GAS SAMPLE CHAMBER, now U.S. Pat. No. 5,163,332, which was a continuation of U.S. application Ser. No. 07/604,615 filed Oct. 26, 1990, now abandoned which was a continuation-in-part of U.S. application Ser. No. 07/503,216 filed Apr. 2, 1990 and issued Oct. 29, 1991 as U.S. Pat. No. 5,060,508 for "Gas Sample Chamber."

BACKGROUND OF THE INVENTION

1. Field of the Invention

The present invention is in the field of gas analyzers and specifically relates to a sample chamber for use in a gas analyzer of the type known as an NDIR (nondispersive infrared) analyzer.

2. The Prior Art

The NDIR technique has long been considered one of the best methods for gas measurement. In addition to being highly specific, the NDIR-gas analyzers are also very sensitive, stable, reliable, and easy to maintain. The major drawback of the NDIR gas measurement technique has been its complicated and expensive implementation.

An NDIR gas analyzer typically includes an infrared source, a motor-driven mechanical chopper to modulate the source so that synchronous detection can be used, a pump to push or pull gas through a sample chamber, a bandpass filter, a sensitive infrared detector plus expensive infrared optics and windows to focus the infrared energy from the source onto the detector. Thus, despite the fact that the NDIR gas measurement technique is one of the best, it has not found wide application because of its complexity and high cost of implementation.

The present invention significantly simplifies the implementation of the NDIR gas measurement technique, and this simplification results in a concomitant reduction in cost, thereby opening dozens of applications for the NDIR technique that were heretofore considered impractical because of cost or complexity.

For example, the sample chamber of the present invention is at the heart of a much faster and sensitive carbon dioxide detector for use in sensing fires, (U.S. Pat. No. 5,053,754 issued Oct. 1, 1991 to the present applicant), and is also at the heart of a ventilation controller or VENTOSTAT (the thermostat of ventilation as described in U.S. patent application No. 07/611,630 filed Jun. 6, 1991 for VENTILATION CONTROLLER by the present inventor), which is highly useful in combatting indoor air pollution by monitoring the concentration of carbon dioxide in the indoor air and bringing in fresh air when the carbon dioxide concentration is excessive.

The present invention for a simplified gas sample chamber provides a novel approach for reducing the complexity of NDIR gas measurement systems by eliminating the need for: expensive optics, mechanical choppers, and a pump for pulling or pushing the gas into the sample chamber. In addition, the sample chamber of the present invention provides a long effective pathlength which increases the detection sensitivity.

In U.S. Pat. No. 4,709,150 issued Nov. 24, 1987 to Burough et al., there is described a gas sample chamber that consists of a tube composed of a porous material such as plastic or a sintered metal. Burough et al. teach that the pore size should be from 0.3 to 100 microns. There is no teaching or suggestion of using the walls of the porous tube as reflective radiation-guiding elements. Perhaps for this reason, the problem of condensation of the gas into droplets on the interior of the sample cell is not addressed.

Burough et al. do not teach or suggest multiple reflections from a specularly-reflective surface. This seriously affects the performance of their system. Without taking advantage of the radiation-collecting ability of the sample chamber, the system of Burough et al. has much poorer radiation collecting ability, leading to a lower signal-to-noise ratio. Furthermore, the system of Burough et al. does not have provision for a long pathlength, and hence the sensitivity of his system suffers in comparison with the present invention.

With regard to the diffusion of gas into the chamber of Burough et al., as compared to the present invention, it is noted that the porous material used in the sample chamber of Burough et al. is several hundreds of microns thick. In contrast, in the present invention, the diffusion into the sample chamber takes place through a semi-permeable membrane which is on the order of 25 to 50 microns thick. Accordingly, it takes much longer for the gas, or changes in the concentration in the gas, to diffuse into the chamber of Burough et al., as compared with the present invention. This greatly lengthens the response time of the chamber of Burough et al., thereby making it a poor choice for a fire detecting sensor, whereas the chamber of the present invention responds very rapidly to changes in the carbon dioxide concentration, and laboratory tests have demonstrated that the sample chamber of the present invention has an extremely fast response time which is highly desirable in a fire detector.

In Japanese Patent Publication (Kokai) No. 59-173734(A), Miyazaki describes an infrared ray gas analysis meter in which radiation proceeds in parallel along a sample cell and a reference cell. These cells have the form of a helical tube.

Miyazaki's system, as disclosed in his patent, falls under the category of a conventional NDIR gas measurement system. Were it not for the fact that the incident radiation undergoes multiple reflections inside both the sample and reference cells, there would be no difference from a conventional NDIR system, and consequently no advantage at all. Miyazaki's design still calls for a mechanical chopper, pumps to direct gases through both the sample and reference cells, and two detectors. Thus, when these factors are taken into consideration, Miyazaki's invention does not come close in simplicity and efficiency to the present invention.

In Japanese Patent Publication (Kokai) No. 63-298031(A), Fujimura discloses the use of a filter, which is required in his invention since the source of radiation and the detectors used in his system reside inside the sample chamber and are thus subject to contamination by the sample.

In U.S. Pat. No. 4,499,379 issued Feb. 12, 1985 to Miyatake et al. and in U.S. Pat. No. 4,501,968 issued Feb. 26, 1985 to Ebi et al., there is described a gas analyzer having a heated sample gas container for containing a sample gas at a temperature at which the component whose concentration is to be determined will emit infrared radiation of a characteristic wavelength. This gas analyzer works on an emission principle and is not a nondispersive infrared absorption analyzer. A heater in the wall of the sample cell heats the sample gas to temperatures of at least 100° C. to cause the gas to radiate infrared. This is said to increase the radiation from a sample of the gas while decreasing the background radiation relative to the radiation from the gas. The internal surface of the sample cell is said to be a mirror surface, but the patents give no reason for this. Since the gas itself is the source of the radiation, which is isotropic, it does not appear that the walls of the chamber would serve to guide the radiation in any useful way.

In U.S. Pat. No. 3,966,439 issued Jun. 29, 1976 to Vennos, there is described a fluid sampling device that includes a pump and that is used for accumulating a sample of particles found in the air, in factories, power plants, mines, etc.

Vennos is not concerned with passing infrared radiation through a gaseous sample to determine its concentration, and thus the filtering system of Vennos is from a nonanalogous art.

Likewise, in U.S. Pat. No. 4,947,578 issued Aug. 14, 1990 to Anderson et al., there is described a controlled release system for an insect attractant. In this patent the attractant vapor is allowed to diffuse through a membrane. Because the pore size is determined by the desired release rate, the use of the membrane by Anderson et al. is not analogous to that of the present invention.

SUMMARY OF THE INVENTION

It is a first objective of the gas sample chamber of the present invention to serve as a light pipe to efficiently conduct radiation from the source through a gas sample to a detector.

It is a second objective of the gas sample chamber of the present invention to selectively keep particles of smoke and dust that are larger than 0.1 micron out of the sample chamber so that they will not cause error in the measurement of the concentration of a particular gas, while at the same time permitting molecules of the gas to freely enter and leave the sample chamber.

In accordance with a preferred embodiment of the invention, the inwardly-facing wall of the sample chamber includes a specularly-reflective surface that serves as a light pipe to conduct radiation introduced at one end of the elongated sample chamber by a source to a detector.

Also in accordance with the present invention, an aperture is included in the wall of the chamber, and this aperture is spanned by a layer of a semi-permeable membrane that keeps particles larger than 0.1 micron from entering the space within the chamber.

It is a third objective of the gas sample chamber of the present invention to function as a multi-channel gas sample chamber.

In accordance with the present invention several detectors equipped with different narrow bandpass interference filters as windows are mounted at the detector end of the sample chamber. By virtue of the fact that the gas sample chamber of the present invention serves as a light pipe to conduct radiation via multiple reflections inside the highly reflective wall, the entire sample chamber is uniformly illuminated with radiation at a slowly decreasing intensity towards the detector end. Thus, at the detector end each of the several mounted detectors essentially receive the same radiation intensity from the common source. Furthermore, each of the common source-detector pair has approximately the same path-length. Thus, if each of the several mounted detectors carries a different narrow bandpass filter that passes radiation which is absorbed by a particular gas present in the gas chamber, the present invention functions as a multi-channel gas sample chamber.

It is a fourth objective of the present gas sample chamber of the present invention to function as a multi-channel gas sample chamber each of which may have the same or different path-lengths.

In accordance with the present invention, several detectors are mounted at various distances from the source in such a way that the gas chamber becomes a multiple-channel gas chamber as explained in the third objective of the present invention disclosed above. Furthermore, the effective path-length of the sample chamber for each of the common-source detector pair is different and depends only upon the distance from the source at which a particular detector is mounted. Thus, if the detectors are mounted at different distances from the source, the gas chamber of the present invention functions as a multi-channel variable pathlength gas sample chamber.

It is a further objective of the invention to provide a gas chamber in which condensation of gases or vapors on the inwardly facing walls of the sample chamber can be prevented.

In accordance with a preferred embodiment of the invention, means are provided for heating the sample chamber so that its temperature is above the dew point of any gas or vapor that might have a tendency to condense on the inwardly-facing wall of the sample chamber.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a side elevational view showing the major parts of a gas analyzer in accordance with the present invention;

FIG. 2 is a diagram showing the path of a typical ray of radiation through the gas sample chamber; and, FIG. 3 is a fractional cross-sectional view of a gas sample chamber in accordance with a preferred embodiment of the present invention;

FIG. 4 is a side elevational cross sectional view of the sample chamber of the present invention in a first preferred embodiment; and, FIG. 5 is a side elevational cross sectional view of the sample chamber of the present invention on a second preferred embodiment.

DETAILED DESCRIPTION OF THE PREFERRED EMBODIMENT

As shown in FIG. 1, a gas analyzer includes a source chamber 12 that contains a source of radiation. The source may be a small incandescent lamp and the radiation may be visible light and/or infrared radiation produced by the lamp. The source chamber 12 is connected to a gas sample chamber 10 that includes a gas sample to be analyzed to determine the concentration of a particular gaseous component. Radiation from the source chamber 12 passes through the gas sample that is contained in the gas sample chamber 10, and thereafter the radiation falls on more than one detector located in the detector chamber 14. The detectors produce electrical signals that represent the intensity of the radiation falling on them. To enhance the sensitivity of the device, it is well known to place a narrow pass band filter in the optical path in front of the detector, so that the detector receives mainly radiation of a wavelength that is strongly absorbed by the gas whose concentration is to be determined. The electrical signals produced by the detectors are applied to an electronic circuit 15 that converts them to signals that represent the concentration of the gas in question.

FIG. 2 is an optical diagram showing the optical path taken by a typical ray 18 emitted by the source 16 as the ray is multiply reflected as it passes down the length of the gas sample chamber, and eventually falls on the detector 20.

FIG. 3 is a fractional cross-sectional view through the gas sample chamber. The body of the gas sample chamber is an elongated hollow tube 21 having an inwardly-facing specularly-reflecting surface 22. In the preferred embodiments, this surface 22 is a unitary portion of the wall of the tube 21, while in alternative embodiments, the surface may be an applied coating or a layer of a specularly-reflective material.

The elongated hollow tube 21 includes at least one aperture, of which the aperture 24 is typical. These apertures serve to permit ambient gases to enter and leave the sample chamber. However, it is not desirable that particles of dust and smoke should be able to enter the chamber freely, and to that end, the aperture 24 is spanned by a sheet 28 of a semi-permeable membrane that keeps out particles of a size greater than 0.1 micron. To achieve high rates of diffusion for particles of size less that 0.1 micron, the sheet 28 of semi-permeable membrane must be quite thin, and therefore it is supported on a supporting mesh 26. In the preferred embodiments, the semi-permeable membrane is composed of silicone rubber.

Because the gas sample chamber is always filled with gas, there is a possibility that if the ambient temperature falls sufficiently, water vapor or one of the other gases in the sample chamber will condense to a liquid state and be deposited in the form of small droplets on the specularly-reflecting surface 22 as well as on the detector 20. This would interfere with the specular reflection that is needed for operation of the sample chamber, and would lead to erroneous results.

To prevent this from happening, in the preferred embodiments, a heater wire 30 is deployed on the gas sample chamber 10. A thermistor 32 measures the temperature of the wall of the sample chamber. Both the thermistor and the heater wire are connected to a heater control circuit 34 which is a servo that operates in the well known way to maintain the sample chamber at a set temperature.

FIG. 4 shows a multi-channel gas sample chamber in accordance with a first preferred embodiment of the present invention.

As described above in connection with FIGS. 1 and 2, radiation from a source 36 progresses down the elongated hollow tube 38 that constitutes the body of the sample chamber by successive specular reflections. Only a very small fraction of the radiation is absorbed on each reflection, making possible the use of long pathlengths if they are needed.

In the first preferred embodiment of FIG. 4, the sample chamber includes a number of apertures of which the aperture 24 is typical. These apertures are spanned by a sheet 28 of a semi-permeable membrane that keeps out particles of a size greater than 0.1 micron. To permit high rates of diffusion of gas molecules through the sheet 28, it must be quite thin, and is supported on a supporting mesh as described in connection with FIG. 3.

The first preferred embodiment of FIG. 4 is characterized by the presence of at least one detector, all located at the end opposite the source. These detectors, exemplified by the detectors 40, 42, 44 are located at detector ports 46, 48, 50, respectively, that extend through the elongated hollow tube at stations spaced around the periphery of the tube 38. As used herein, each detector includes a filter that passes only radiation having particular chosen wavelengths. For example, filter 41 is included in detector 40. Each of the filters has its own spectral characteristic. In a preferred embodiment each of the filters has a spectral characteristic that enables the associated detector to be effective in detecting a particular component of a gas being analyzed.

In one example of the preferred embodiment of FIG. 4, the tube 38 has a square cross section, and each face includes a detector port.

In another example of the preferred embodiment of FIG. 4, a detector port 52 is formed in a wall 54 that spans the end of the tube 38.

In a refinement of the first preferred embodiment, the five detectors of FIG. 4 may be encapsulated in a plastic material to form a cap that fits over the end of the tube 38.

Thus, in accordance with the first preferred embodiment of FIG. 4, all of the detectors and their respective detector ports are located at or adjacent one end of the tube 38.

In contrast, in the second preferred embodiment of FIG. 5, the various detectors 56, 58, 60 and their respective detector ports, 62, 64 and 66 are located at stations spaced along the length of the tube 38.

This second preferred embodiment is useful in reducing the dynamic range required of the electronic circuitry when the detectors are sampled sequentially. This is achieved by using shorter pathlengths for the more strongly absorbing gas components and longer pathlengths for the weakly absorbing gas components.

As with the first preferred embodiment, one 68 of the detectors may be located at the end of the tube.

Thus, there has been described a gas sample chamber in the form of an elongated tubular member having an inwardly-facing specularly-reflective surface that conducts radiation through the gas from a detector to a source. Dust and smoke particles are kept out of the sample chamber by a sheet of semi-permeable membrane that spans apertures that extend through the tubular wall of the sample chamber. The wall of the sample chamber may be heated to prevent condensation of gaseous components in the chamber, and in the preferred embodiment, a preset temperature is maintained by a servo.

In a first preferred embodiment a number of detectors are located at or adjacent the end of the sample chamber opposite a source of radiation, while in a second preferred embodiment, a number of detectors are spaced along the length of the sample chamber.

The foregoing detailed description is illustrative of two embodiments of the invention, and it is to be understood that additional embodiments thereof will be obvious to those skilled in the art. The embodiments described herein together with those additional embodiments are considered to be within the scope of the invention.

What is claimed is:

1. A multi-channel diffusion-type gas sample chamber for conducting radiation through a gas, comprising in combination:

an elongated hollow tube having a wall, composed of a gastight material, and having an inwardly-facing specularly-reflective surface that conducts radiation introduced at one end of said elongated hollow tube toward the other end with high efficiency by means of multiple reflections from said inwardly-facing specularly-reflective surface, said elongated hollow tube having a plurality of apertures extending through the wall and located intermediate the ends of said elongated hollow tube, said elongated hollow tube further having a plurality of detector ports extending through the wall of said elongated hollow tube; and, a sheet of a semi-permeable membrane covering each of said plurality of apertures, said sheet permitting airborne particles smaller than a specific size to diffuse through it into and out of the space within said elongated hollow tube and preventing airborne particles larger than said specific size from entering said space.

2. The multi-channel diffusion-type gas sample chamber of claim 1 further comprising in combination: means for heating said specularly-reflective surface to a temperature above the dew point of the gas to prevent condensation on said specularly-reflective surface.

3. The multi-channel gas sample chamber of claim 2 wherein said plurality of detector ports are spaced around the periphery of said elongated hollow tube adjacent one end of it.

4. The multi-channel gas sample chamber of claim 2 wherein said plurality of detector ports are spaced along the length of said elongated hollow tube.

5. The multi-channel gas sample chamber of claim 1 wherein said plurality of detector ports are spaced around the periphery of said elongated hollow tube adjacent one end of it.

6. The multi-channel gas sample chamber of claim 1 wherein said plurality of detector ports are spaced along the length of said elongated hollow tube.

* * * * *